United States Patent

Maeda et al.

[11] Patent Number: 5,595,952
[45] Date of Patent: Jan. 21, 1997

[54] CRYSTALLINE ALUMINUM ORGANOPHOSPHATE

[75] Inventors: Kazuyuki Maeda; Yoshimichi Kiyozumi; Fujio Mizukami, all of Tsukuba, Japan

[73] Assignee: Director-General of Agency of Industrial Science and Technology, Tokyo, Japan

[21] Appl. No.: 401,914

[22] Filed: Mar. 9, 1995

[30] Foreign Application Priority Data

Mar. 11, 1994 [JP] Japan ................................. 6-068026

[51] Int. Cl.$^6$ ................................................. B01J 27/14
[52] U.S. Cl. ........................... 502/162; 502/155; 502/208
[58] Field of Search ............................... 502/155, 162, 502/208, 355, 164

[56] References Cited

U.S. PATENT DOCUMENTS

| | | | |
|---|---|---|---|
| 4,310,440 | 1/1982 | Wilson et al. | 502/208 |
| 4,440,871 | 4/1984 | Lok et al. | 502/214 |
| 4,554,143 | 11/1985 | Messina et al. | 423/306 |
| 4,960,745 | 10/1990 | Johnson | 502/155 |

Primary Examiner—Glenn A. Caldarola
Attorney, Agent, or Firm—Birch, Stewart, Kolasch & Birch, LLP

[57] ABSTRACT

There is disclosed a crystalline aluminum organophosphate stable against heating, composed of a skeleton structure having micropores therein and represented by the following formula (I) in chemical composition:

formula (I)

$$[(Al_2O_3) \cdot (RPO_2)_x]$$

wherein R represents an alkyl group, and x is such a number that $2.0 \leq x \leq 3.6$. The crystalline aluminum organophosphate is a microporous material having an inner wall of pores that is hydrophobic and has a flexibility, and it may be used as a separative adsorbent, a catalyst, a packing material for chromatography, and the like.

8 Claims, No Drawings

CRYSTALLINE ALUMINUM ORGANOPHOSPHATE

FIELD OF THE INVENTION

The present invention relates to porous crystalline aluminum organophosphates that can be used, for example, as separative adsorbents for organic materials, as catalysts, and as packing materials for chromatography.

BACKGROUND OF THE INVENTION

Zeolites, which are typical porous materials, are aluminosilicates wherein a silicate skeleton has developed three-dimensionally. Zeolites have molecular-size pores and a stereoselective adsorptive action, so that they have a function as molecular sieves. In addition to tens of naturally occurring zeolites, many kinds of zeolites have been synthesized hitherto and are extensively used in the fields of catalysts, separative adsorbents, ion exchangers, and the like.

Aluminophosphates, $AlPO_4$, which are like zeolites and are anhydrous neutral salts in that they do not contain silica, can have an isoelectronic structure similar to that of silica. Thus, like zeolites wherein a silicate skeleton has developed three-dimensionally, aluminophosphates can have a skeleton structure of $[AlO_4]$ tetrahedral structures and $[PO_4]$ tetrahedral structures arranged alternately. S. T. Wilson et al. have reported that hydrothermal reactions, in which a variety of amines have been added as organic templates, can selectively produce aluminosilicate molecular sieves having more than 10 different skeleton structures (U.S. Pat. No. 4,310,440; 1982). These aluminophosphates have micropores of effective pore diameter 0.3 to 1.0 nm, and they are useful as adsorbents and porous carriers used to support catalysts. Besides these, many similar aluminophosphates having micropores have been reported.

Further, there are reports of compounds (SAPO) in which part of aluminum atoms have been substituted by silicon atoms in an isomorphous manner (U.S. Pat. No. 4,440,871; 1984), as well as many useful AlPO substitution products (U.S. Pat. No. 4,554,143; 1985), in which isomorphous substitution with transition metals and the like has been made, and they are shown to be used as ion exchanges, catalysts, and the like.

Since, in these molecular sieves, however, the inner wall of the pores is composed of oxygen atoms, generally many of the molecular sieves are hydrophilic and the pore structure is poor in flexibility. These properties narrow the range of the use of these molecular sieves as separating/adsorbing materials for nonpolar organic materials. The size and shape of the pores of these conventional molecular sieves are all determined by the skeleton of the inorganic oxide. Although the size and shape of the pores can be controlled roughly, it is difficult to control the shape of the pores precisely.

SUMMARY OF THE INVENTION

An object of the present invention is to provide a crystalline aluminum salt whose pore size and pore shape can be controlled.

Other and further objects, features, and advantages of the invention will appear more fully from the following description.

DETAILED DESCRIPTION OF THE INVENTION

Taking the above conventional problems into account, the present inventors have keenly studied crystalline aluminum salts whose pore size and pore shape can be controlled. As a result, it has been found that, by mixing various organophosphate compounds and aluminum raw materials with water and/or a solvent, and heating the mixtures in a pressure vessel under autogenous pressure, a series of crystalline aluminum organophosphates can be obtained wherein organic groups forming part of the skeleton are arranged in the pore spaces that form the inorganic skeleton. The present invention has been completed based on this finding.

That is, the present invention provides:

(1) a crystalline aluminum organophosphate stable against heating, composed of a skeleton structure having micropores therein and represented by the following formula (I) in chemical composition:

formula (I)

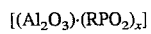

wherein R represents an alkyl group (e.g., a lower alkyl group, such as methyl and propyl) linked to the phosphorus atom, and x is such a number that $2.0 \leq x \leq 3.6$, (2) the crystalline aluminum organophosphate as stated in the above (1), wherein R in formula (I) represents a methyl group, (3) the crystalline aluminum organophosphate as stated in the above (1) or (2), wherein the skeleton structure has uniform micropores having a diameter in the range of about 0.26 to about 1.2 nm, (4) the crystalline aluminum organophosphate as stated in the above (1) or (2), which gives a powder X-ray diffraction pattern containing at least diffraction interplanar spacings d shown in the following Table 1:

TABLE 1

| 2θ | d | Relative intensity |
|---|---|---|
| 7.15–7.45 | 12.4–11.8 | 1000 |
| 12.5–12.8 | 7.09–6.91 | 40–300 |
| 19.2–19.5 | 4.62–4.54 | 60–250 |
| 21.85–22.15 | 4.07–4.00 | 80–300 |
| 25.25–25.55 | 3.53–3.48 | 5–50 |
| 26.35–26.65 | 3.39–3.34 | 5–50 |
| 28.4–28.7 | 3.15–3.11 | 5–50 |
| 33.7–34.0 | 2.66–2.63 | 5–50 |
| 39.15–39.45 | 2.30–2.28 | 5–50 | and wherein said x is such that $2.4 \leq x \leq 3.6$, (5) the crystalline aluminum organophosphate as stated in the above (1) or (2), which gives a powder X-ray diffraction pattern containing at least diffraction interplanar spacings d shown in the following Table 2:

TABLE 2

| 2θ | d | Relative intensity |
|---|---|---|
| 7.05–7.35 | 12.6–12.0 | 1000 |
| 11.35–11.65 | 7.80–7.59 | 10–50 |
| 12.25–12.55 | 7.21–7.03 | 10–50 |
| 18.85–19.15 | 4.71–4.63 | 30–200 |
| 20.9–21.2 | 4.25–4.18 | 10–50 |
| 21.6–21.9 | 4.12–4.05 | 30–200 |

TABLE 2-continued

| 2θ | d | Relative intensity |
|---|---|---|
| 24.8–25.1 | 3.59–3.54 | 10–50 |
| 27.9–28.2 | 3.20–3.15 | 10–50 | and wherein said x is such that 2.4≦x≦3.6, and (6) the crystalline aluminum organophosphate as stated in the above (1) or (2), which gives a powder X-ray diffraction pattern containing at least diffraction interplanar spacings d shown in the following Table 3:

TABLE 3

| 2θ | d | Relative intensity |
|---|---|---|
| 9.1–9.4 | 9.76–9.44 | 1000 |
| 11.3–11.6 | 7.83–7.62 | 30–200 |
| 18.3–18.6 | 4.85–4.76 | 20–100 |
| 19.9–20.2 | 4.46–4.39 | 5–70 |
| 21.4–21.7 | 4.15–4.09 | 5–70 |
| 23.7–24.0 | 3.76–3.70 | 60–250 |
| 24.0–24.3 | 3.71–3.65 | 50–250 |
| 31.7–32.0 | 2.82–2.79 | 20–150 | and wherein said x is such that 2.0≦x≦3.3.

In this specification, by "an aluminum organophosphate" is meant an aluminum salt of an oxygen acid of phosphorus that has organic groups linked to phosphorus atoms.

In the crystalline aluminum organophosphate of the present invention, by linking organic groups to an inorganic skeleton, an in-pore structure is constructed. If only an inorganic oxide is used, the pore structure is basically determined by the number of oxygen atoms constituting the pore wall (inner wall of pores). By introducing the organic groups that constitute part of the skeleton, a pore structure higher in degree of freedom becomes possible to design, and also the hydrophobic nature of the pore wall can be controlled. As an inorganic oxide having organic groups linked thereto, organic phosphoric acids, including particularly phosphonic acids, are materials suitable for the above purposes. The reasons are that the organic groups can be designed easily and such acids can be synthesized readily, and because the P-C bond is a covalent bond, which is therefore stable against heat and will thus generally allow the organic phosphoric acids to withstand heating in a pressure container.

In the production of the crystalline aluminum organophosphate of the present invention, as the organic phosphoric acid of a phosphorus source, an alkylphosphonic acid represented by the following formula:

$$RPO_3H_2$$

wherein R represents an alkyl group, and preferably a lower alkyl group, such as a methyl group, that is linked to the phosphorus atom—for example methylphosphonic acid—is used in order to increase the hydrophobic nature of the pore wall. Derivatives of these organic phosphoric acids, such as their salts and esters, can be used as a phosphorus source.

On the other hand, as the aluminum source, alumina hydrates, such as pseudoboehmite, are most preferable. Besides them, use can be made of aluminum hydroxides, such as gibbsite and bayerite, and aluminum compounds that can be converted to alumina hydrates easily by means of hydrolysis or the like, such as aluminum salts, including aluminum nitrate and aluminum chloride; aluminum alkoxides, including aluminum isopropoxide; or aluminates.

In the system of producing the crystalline aluminum organophosphate of the present invention from the above aluminum source and phosphorus source, as a solvent generally used in the reaction, water is most desirable. The amount of water to be used is such that the molar ratio of water to the aluminum in the aluminum source is generally from 4:1 to 200:1, and preferably from 30:1 to 100:1. Instead of using water singly, some other suitable additive may be added in addition to water, or instead of water itself the suitable additive may be used as a solvent to carry out the synthesis. Such an additive includes, for example, mineral acids; carboxylic acids, such as acetic acid and lauric acid; alcohols; glycols, such as triethylene glycol; and ethers, such as dioxane.

These raw materials may be suitably stirred; they may be dispersed with ultrasonic waves; or they may be allowed to stand without stirring, so that a raw material solution or gel is obtained.

The reaction of forming the skeleton of the aluminum organophosphate of the present invention is carried out by hydrothermal synthesis in a pressure-resistant vessel inert to the reaction system. If the temperature at which the reaction is carried out is too low, the crystallization of the aluminum organophosphate does not proceed satisfactorily, whereas if the reaction temperature is too high, the heat stability of the skeleton structure may be compromised. The reaction temperature is generally 100° to 350° C., preferably 130° to 250° C. Although the reaction time is not particularly restricted, the reaction time is generally 30 min or over, and preferably in the range of 4 hours to 30 days, because if the reaction time is too short, the crystallization does not proceed satisfactorily. Further, the reaction pressure is suitably a pressure that is autogenously attained in the pressure-resistant vessel having a certain volume under the above reaction conditions. In the specification, such a pressure is referred to as "autogenous pressure." The ratio of the phosphorus source to the aluminum source to be used is such that the molar ratio of the phosphorus in the phosphorus source to the aluminum in the aluminum source is generally from 1.0:1.0 to 1.8:1.0, and preferably from 1.2:1.0 to 1.6:1.0.

By separating the solid obtained by the hydrothermal synthesis from the liquid phase by means of filtration, centrifugation, or the like, the crystalline aluminum organophosphate can be obtained. At that time, sometimes the unreacted phosphorus source and the additive remain, and therefore it is important to wash the crystalline aluminum organophosphate well with water. Further, when components sparingly soluble in water are left over, desirably the crystalline aluminum organophosphate is washed with an aqueous dilute ammonia or acid solution or a suitable organic solvent.

The thus obtained solid contains the water, the added organic material, and the like, in the micropores formed in the skeleton, and generally it is low in separative adsorptivity if the solid is in an unsatisfactorily dried state. Therefore, it is required to heat the solid in an atmosphere, for example, of dry air, nitrogen, or argon, or in a vacuum, to remove contents in the pores. To remove the contents, such as water, generally heat treatment at least about 200° C. is required. Accordingly, if the crystalline structure is thermally broken at that temperature and the skeleton structure cannot be retained, the aluminum organophosphate is not practical as a material for separative adsorption that makes use of the microchannel structure. The crystalline aluminum organophosphate of the present invention is high in stability against heating, and the crystalline structure is not changed by even heating to at least 200° C. Generally, although the P-C bond is a covalent bond and is thermally stable, the P-C bond is gradually broken by heat treatment at about 400° to 600° C. or over.

The crystalline aluminum organophosphate of the present invention is microporous, and the specific surface area thereof is generally 40 to 600 $m^2/g$, preferably 100 to 600 $m^2/g$, after heat treatment at 200° to 600° C.

Preferably, the pores of the crystalline aluminum organophosphate of the present invention have a diameter in the range of about 0.26 to about 1.2 nm, and more preferably in the range of about 0.4 to about 1.2 nm.

The crystalline aluminum organophosphate of the present invention is a crystalline aluminum organophosphate, in which organic groups constituting part of the skeleton are arranged in the pore spaces that form the inorganic skeleton. According to the present invention, a microporous material having hydrophobic and flexible micropore walls can be obtained. Further, by changing the reaction conditions, crystalline aluminum organophosphates different in inorganic skeleton structure can be obtained, so that crystalline aluminum organophosphates different in characteristics, such as hydrophobic nature and wall surface shape of the pore walls, can be obtained. The crystalline aluminum organophosphate of the present invention has a variety of applications, for example, in a separative adsorbent, a catalyst, and a packing material for chromatography. The crystalline aluminum organophosphate of the present invention also has applications in the field of an excellent nonlinear optical material and an electronic material, by using the pore spaces, which are modified with organic groups, as reaction vessels. That is, by making organic- or inorganic-materials, that does not necessarily have excellent optical or electrical characteristics as it solely is, arranged in the pore spaces, new material having specific characteristics can be obtained.

The present invention will now be described in more detail with reference to the following Examples, but the present invention is not restricted to them.

In the following Examples, processes of producing individual aluminum organophosphates of the present invention, as well as their characteristics, are described. The phase of the crystalline aluminum organophosphate compound of the present invention obtained in each Example is called AlMepO-$\chi$ (wherein $\chi$ is a Greek letter particular to each compound phase). The used reagents were pseudoboehmite (manufactured by CONDEA CHEMIE; trade name, PURAL SCF; $Al_2O_3$ content: 74.44%), aluminum hydroxide (manufactured by Fuji Kagaku, gibbsite phase), and methylphosphonic acid (manufactured by ALDRICH, 98%). The powder X-ray diffraction pattern was obtained by step scanning with a spacing of 0.01°, using an MXP18, manufactured by MAC SCIENCE, using a Cu-K$\alpha$ ray at 40 kV and 100 mA. With respect to the chemical analysis, an organic elemental analysis was carried out for C and H; and an ICP emission spectrochemical analysis, in which the solution was obtained by decomposing a sample of the solid with aqua regia, was used for Al and P. The nitrogen adsorption isotherm was measured using BERLSORP 36, manufactured by NIHON BELL.

EXAMPLE 1

Preparation of AlMepO-α

(a) 6.82 g of water was added to 0.685 g of boehmite and 0.978 g of methylphosphonic acid; then they were placed, to stand still, in an internal cylinder of Teflon (trade name) in a stainless steel pressure-resistant vessel, and the mixture in the vessel was heated under autogenous pressure in a constant-temperature bath at 220° C. for 48 hours, followed by cooling to room temperature. The resulting solid reaction product was a mixture of needle crystals and solid masses. The suspended needle crystals were taken out by filtration, so that the solid masses adhered to the bottom of the Teflon inner cylinder would not be broken, and then the needle crystals were washed with water and were dried in air, to obtain 0.06 g of aluminum methylphosphonate. The obtained product (the above-mentioned needle crystals) gave a powder X-ray diffraction pattern characterized by the intensity data shown in Table 4. The chemical analysis of the product showed that it contained 11.2% by weight of C, 2.6% by weight of H, 15.9% by weight of Al, and 27.8% by weight of P; and the P/Al molar ratio was 1.52. The product was named AlMepO-α.

TABLE 4

| 2θ | d | Relative intensity |
| --- | --- | --- |
| 7.30 | 12.099 | 1000 |
| 12.64 | 6.9970 | 62 |
| 14.61 | 6.0577 | 5 |
| 17.94 | 4.9403 | 5 |
| 19.36 | 4.5809 | 140 |
| 20.84 | 4.2588 | 8 |
| 22.00 | 4.0369 | 159 |
| 24.35 | 3.6524 | 13 |
| 25.41 | 3.5023 | 21 |
| 26.49 | 3.3619 | 31 |
| 28.52 | 3.1270 | 23 |
| 33.87 | 2.6444 | 22 |
| 35.49 | 2.5273 | 15 |
| 38.58 | 2.3316 | 10 |
| 39.29 | 2.2912 | 27 |

(b) A part of the crystalline product obtained in the above (a) was baked in air for 2 hours at about 400° C. The baked product gave essentially the same powder X-ray diffraction pattern as that of the product in the above (a).

(c) After a part of the crystalline product obtained in the above (a) was heat-treated in a vacuum for 6 hours at about 400° C., the nitrogen adsorption isotherm at 77 K was measured. The measurement gave an adsorption isotherm characteristic of the compound having micropores, in which isotherm the rise at a low-pressure section was remarkable. From the adsorption isotherm, it was estimated that the Langmuir's specific surface area was 263 $m^2/g$, and from the t-plot, which was derived by using a standard isotherm, it was estimated that the effective pore diameter was about 0.7 nm.

EXAMPLE 2

Preparation of AlMepO-α

6.82 g of water was added to 0.685 g of boehmite and 1.47 g of methylphosphonic acid; then they were placed, to stand still, in an internal cylinder of Teflon in a stainless steel pressure-resistant vessel, and the mixture in the vessel was heated under autogenous pressure in a constant-temperature bath at 160° C. for 48 hours, followed by cooling to room temperature. The resulting solid reaction product was a mixture of needle crystals and solid masses. Only the suspended needle crystals were taken out by filtration, so that the solid masses adhered to the bottom of the Teflon inner cylinder would not be broken, and then the needle crystals were washed with water and were dried in air, to obtain 0.49 g of aluminum methylphosphonate. The major phase in the product gave essentially the same powder X-ray diffraction pattern as that in Example 1. The product also contained a small amount of a crystalline impurity having a phase (AlMepO-β mentioned below) that gave essentially the same powder X-ray diffraction pattern as that in Example 4 mentioned below.

EXAMPLE 3

Preparation of AlMepO-α

0.685 g of boehmite, 1.47 g of methylphosphonic acid, and 22.53 g of triethylene glycol were mixed, and the mixture was stirred for 1 hour, to obtain a dispersion. Then the dispersion was placed in an internal cylinder of Teflon in a stainless steel pressure-resistant vessel, which was placed in turn in a constant-temperature bath, and the dispersion in the vessel was heated under autogenous pressure at 220° C. for 48 hours, followed by cooling to room temperature. The resulting solid reaction product was a mixture of needle crystals and solid masses. Only the suspended needle crystals were scooped out, so that the solid masses adhered to the bottom of the Teflon inner cylinder would not be broken, and then the needle crystals were washed with water and were dried in air, to obtain 1.54 g of aluminum methylphosphonate. This product gave essentially the same powder X-ray diffraction pattern as that in Example 1. The product also contained small amounts of crystalline impurities having phases (AlMepO-β and AlMepO-δ mentioned below) that gave essentially the same powder X-ray diffraction patterns as those in Examples 4 and 9 mentioned below.

In this specification, the crystalline aluminum methylphosphonate that is classified as the above AlMepO-α is a crystalline aluminum organophosphate that has a skeleton structure whose chemical composition is represented by the following formula:

$$[(Al_2O_3) \cdot (MePO_2)_x]$$

wherein Me represents a methyl group linked directly to the phosphorus atom, and x is such a number that $2.4 \leq x \leq 3.6$, and the crystalline aluminum methylphosphonate gives a characteristic powder X-ray diffraction pattern containing at least d (diffraction interplanar spacings) shown in the following Table 5.

TABLE 5

| 2θ | d | Relative intensity |
|---|---|---|
| 7.15–7.45 | 12.4–11.8 | 1000 |
| 12.5–12.8 | 7.09–6.91 | 40–300 |
| 19.2–19.5 | 4.62–4.54 | 60–250 |
| 21.85–22.15 | 4.07–4.00 | 80–300 |
| 25.25–25.55 | 3.53–3.48 | 5–50 |
| 26.35–26.65 | 3.39–3.34 | 5–50 |
| 28.4–28.7 | 3.15–3.11 | 5–50 |
| 33.7–34.0 | 2.66–2.63 | 5–50 |
| 39.15–39.45 | 2.30–2.28 | 5–50 |

EXAMPLE 4

Preparation of AlMepO-β

(a) 0.685 g of boehmite, 1.47 g of methylphosphonic acid, 0.441 g of dioxane, and 6.72 g of water were mixed, and the resulting mixture was stirred for 1 hour, to obtain a uniform dispersion. Then the dispersion was placed in an internal cylinder of Teflon in a stainless steel pressure-resistant vessel, which was placed in turn in a constant-temperature bath, and the dispersion in the vessel was heated under autogenous pressure at 160° C. for 48 hours. After cooling to room temperature, the resulting solid reaction product was filtered, washed with water, and dried in air, to obtain 1.54 g of aluminum methylphosphonate. The solid product was all needle crystals. This product gave a powder X-ray diffraction pattern characterized by the intensity data shown in Table 6. The chemical analysis of the product showed that it contained 11.2% by weight of C, 2.5% by weight of H, 15.2% by weight of Al, and 27.6% by weight of P; and the P/Al molar ratio was 1.58. The product was named AlMepO-β.

TABLE 6

| 2θ | d | Relative intensity |
|---|---|---|
| 7.18 | 12.302 | 1000 |
| 10.84 | 8.1347 | 2 |
| 11.49 | 7.6947 | 20 |
| 12.42 | 7.1205 | 14 |
| 12.99 | 6.8093 | 11 |
| 14.60 | 6.0618 | 3 |
| 16.29 | 5.4366 | 6 |
| 17.79 | 4.9814 | 8 |
| 17.99 | 4.9266 | 6 |
| 18.40 | 4.8177 | 9 |
| 19.00 | 4.6668 | 63 |
| 19.37 | 4.5786 | 7 |
| 21.05 | 4.2168 | 14 |
| 21.73 | 4.0864 | 84 |
| 22.25 | 3.9921 | 4 |
| 24.49 | 3.6317 | 12 |
| 24.94 | 3.5671 | 23 |
| 28.08 | 3.1751 | 20 |
| 33.20 | 2.6962 | 6 |

(b) A part of the crystalline product obtained in the above (a) was baked in air for 2 hours at about 350° C. The baked product gave essentially the same powder X-ray diffraction pattern as that of the product in the above (a).

(c) After a part of the crystalline product obtained in the above (a) was heat-treated in a vacuum for 6 hours at about 350° C., the nitrogen adsorption isotherm at 77 K was measured. The measurement gave an adsorption isotherm characteristic of the compound having micropores, in which isotherm the rise at a low-pressure section was remarkable. From the adsorption isotherm, it was estimated that the Langmuir's specific surface area was 166 m²/g, and from the t-plot, which was derived by using a standard isotherm, it was estimated that the effective pore diameter was about 0.9 nm.

EXAMPLE 5

Preparation of AlMepO-β

0.685 g of boehmite, 1.47 g of methylphosphonic acid, 0.300 g of acetic acid, and 6.72 g of water were mixed, and the resulting mixture was stirred for 1 hour, to obtain a uniform dispersion. Then the dispersion was placed in an internal cylinder of Teflon in a stainless steel pressure-resistant vessel, which was placed in turn in a constant-temperature bath, and the dispersion in the vessel was heated under autogenous pressure at 160° C. for 48 hours. After cooling to room temperature, the resulting solid reaction product was filtered, washed with water, and dried in air, to obtain 1.20 g of aluminum methylphosphonate. The solid product was all needle crystals. This product gave essentially the same powder X-ray diffraction pattern as that in Example 4.

EXAMPLE 6

Preparation of AlMepO-β

0.685 g of boehmite, 1.47 g of methylphosphonic acid, and 6.72 g of water were mixed and stirred for 5 min. Then the mixture was placed in an internal cylinder of Teflon in a stainless steel pressure-resistant vessel, which was placed in turn in a constant-temperature bath, and the mixture in the vessel was heated under autogenous pressure at 160° C. for 96 hours. After cooling to room temperature, the resulting solid reaction product was filtered, washed with water, and dried in air, to obtain 0.86 g of aluminum methylphosphonate. The solid product was all needle crystals. The major phase in the product gave essentially the same powder X-ray diffraction pattern as that in Example 4. The product also contained small amounts of crystalline impurities having phases (AlMepO-α and AlMepO-δ) that gave essentially the same powder X-ray diffraction patterns as those in Example 1 and 9.

EXAMPLE 7

Preparation of AlMepO-β

0.685 g of boehmite, 1.47 g of methylphosphonic acid, 1.00 g of lauric acid, and 6.63 g of water were mixed and stirred for 2 hours. Then the mixture was placed in an internal cylinder of Teflon in a stainless steel pressure-resistant vessel, which was placed in turn in a constant-temperature bath, and the mixture in the vessel was hated under autogenous pressure at 160° C. for 60 hours. After cooling to room temperature, the resulting solid reaction product was filtered, washed well with benzene, and dried in air, to obtain 1.63 g of aluminum methylphosphonate. The product gave essentially the same powder X-ray diffraction pattern as that in Example 4.

EXAMPLE 8

Preparation of AlMepO-β

0.780 g of aluminum hydroxide, 1.47 g of methylphosphonic acid, and 6.64 g of water were mixed and stirred for 1 hour. Then the mixture was placed in an internal cylinder of Teflon in a stainless steel pressure-resistant vessel, which was placed in turn in a constant-temperature bath, and the mixture in the vessel was heated under autogenous pressure at 160° C. for 48 hours. After cooling to room temperature, suspended needle crystals were scooped out, washed with water, and dried in air, to obtain 0.97 g of aluminum methylphosphonate. The product gave essentially the same powder X-ray diffraction pattern as that in Example 4, and the product also contained a phase that gave essentially the same powder X-ray diffraction pattern as that in Example 1.

In this specification, the crystalline aluminum methylphosphonate that is classified as AlMepO-β is a crystalline aluminum organophosphate that has a basic skeleton structure whose chemical composition is represented by the following formula:

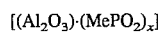

wherein Me represents a methyl group linked directly to the phosphorus atom, and x is such a number that $2.4 \leq x \leq 3.6$, and the crystalline aluminum methylphosphonate gives a characteristic powder X-ray diffraction pattern containing at least d-spacings shown in the following Table 7.

TABLE 7

| 2θ | d | Relative intensity |
|---|---|---|
| 7.05–7.35 | 12.6–12.0 | 1000 |
| 11.35–11.65 | 7.80–7.59 | 10–50 |
| 12.25–12.55 | 7.21–7.03 | 10–50 |
| 18.85–19.15 | 4.71–4.63 | 30–200 |
| 20.9–21.2 | 4.25–4.18 | 10–50 |
| 21.6–21.9 | 4.12–4.05 | 30–200 |
| 24.8–25.1 | 3.59–3.54 | 10–50 |
| 27.9–28.2 | 3.20–3.15 | 10–50 |

EXAMPLE 9

Preparation of AlMepO-δ

(a) 0.685 g of boehmite, 1.47 g of methylphosphonic acid, and 6.72 g of water were mixed, and the resulting mixture was stirred for 1 hour, to obtain a uniform dispersion. Then the dispersion was placed in an internal cylinder of Teflon in a stainless steel pressure-resistant vessel, which was placed in turn in a constant-temperature bath, and the dispersion in the vessel was heated under autogenous pressure at 220° C. for 48 hours. After cooling to room temperature, the resulting solid reaction product was filtered, washed with water, and dried in air, to obtain 1.17 g of aluminum methylphosphonate. This product gave a powder X-ray diffraction pattern characterized by the intensity data shown in Table 8, except that a small amount of a crystalline impurity gave essentially the same powder X-ray diffraction pattern as that in Example 4. The chemical analysis of the product showed that it contained 10.0% by weight of C, 2.9% by weight of H, 15.0% by weight of Al, and 23.9% by weight of P; and the P/Al molar ratio was 1.39. The product was named AlMepO-δ.

TABLE 8

| 2θ | d | Relative intensity |
|---|---|---|
| 9.21 | 9.5942 | 1000 |
| 11.45 | 7.7215 | 50 |
| 11.74 | 7.5313 | 19 |
| 18.44 | 4.8073 | 41 |
| 19.04 | 4.6573 | 10 |
| 20.05 | 4.4248 | 20 |
| 21.04 | 4.2188 | 7 |
| 21.56 | 4.1182 | 19 |
| 22.99 | 3.8652 | 7 |
| 23.84 | 3.7293 | 53 |
| 24.15 | 3.6821 | 30 |
| 24.50 | 3.6302 | 16 |
| 28.91 | 3.0857 | 9 |
| 31.88 | 2.8047 | 32 |
| 38.35 | 2.3451 | 18 |

(b) A part of the crystalline product obtained in the above (a) was baked in air for 2 hours at about 450° C. The baked product gave essentially the same powder X-ray diffraction pattern as that of the product in the above (a).

EXAMPLE 10

Preparation of AlMepO-δ

0.685 g of boehmite, 1.47 g of methylphosphonic acid, and 6.72 g of water were mixed, and the resulting mixture was stirred for 1 hour. Then the mixture was placed in an internal cylinder of Teflon in a stainless steel pressure-resistant vessel, which was placed in turn in a constant-temperature bath, and the mixture in the vessel was heated under autogenous pressure at 160° C. for 96 hours. After cooling to room temperature, the resulting solid reaction product of needle crystals was washed off well with water. Then the solid adhered to the wall surface of the internal cylinder of Teflon was scraped off and dried in air, to obtain 0.10 g of aluminum methylphosphonate. This product gave essentially the same powder X-ray diffraction pattern as that in Example 9.

EXAMPLE 11

Preparation of AlMepO-δ

0.348 g of boehmite, 0.981 g of methylphosphonic acid, and 5.31 g of water were mixed, and the resulting mixture was stirred for 1 hour, to obtain a uniform dispersion. Then the dispersion was placed in an internal cylinder of Teflon in a stainless steel pressure-resistant vessel, which was placed in turn in a constant-temperature bath, and the dispersion in the vessel was heated under autogenous pressure at 200° C. for 100 hours. After cooling to room temperature, the resulting solid reaction product was filtered, washed with water, and dried in air, to obtain 0.41 g of aluminum methylphosphonate. The major phase of this product gave essentially the same powder X-ray diffraction pattern as that in Example 9. As a small amount of a crystalline impurity, this product also contained a phase that gave essentially the same powder X-ray diffraction pattern as that in Example 4.

In this specification, the crystalline aluminum methylphosphonate that is classified as AlMepO-δ is a crystalline aluminum organophosphate that has a basic skeleton structure whose chemical composition is represented by the following formula:

$$[(Al_2O_3) \cdot (MePO_2)_x]$$

wherein Me represents a methyl group linked directly to the phosphorus atom, and x is such a number that $2.0 \leq x \leq 3.3$, and the crystalline aluminum methylphosphonate gives a characteristic powder X-ray diffraction pattern containing at least d-spacings shown in the following Table 9.

TABLE 9

| 2θ | d | Relative intensity |
|---|---|---|
| 9.1–9.4 | 9.76–9.44 | 1000 |
| 11.3–11.6 | 7.83–7.62 | 30–200 |
| 18.3–18.6 | 4.85–4.76 | 20–100 |
| 19.9–20.2 | 4.46–4.39 | 5–70 |
| 21.4–21.7 | 4.15–4.09 | 5–70 |
| 23.7–24.0 | 3.76–3.70 | 60–250 |
| 24.0–24.3 | 3.71–3.65 | 50–250 |
| 31.7–32.0 | 2.82–2.79 | 20–150 |

Reference Example (a) 0.685 g of boehmite, 1.47 g of methylphosphonic acid, and 6.72 g of water were mixed, and the resulting mixture was stirred for 1 hour, to obtain a uniform dispersion. Then the dispersion was transferred into a flask with a condenser tube and was refluxed for 48 hours in an oil bath at 120° C. After cooling to room temperature, the solid reaction product was filtered, washed with water, and dried in air. The obtained solid product gave a powder X-ray diffraction pattern characterized by the intensity data shown in Table 10.

TABLE 10

| 2θ | d | Relative intensity |
|---|---|---|
| 9.70 | 9.1100 | 1000 |
| 14.58 | 6.0702 | 46 |
| 16.42 | 5.3938 | 27 |
| 18.68 | 4.7461 | 36 |
| 21.70 | 4.0919 | 45 |
| 23.42 | 3.7951 | 84 |
| 25.88 | 3.4398 | 24 |
| 29.30 | 3.0456 | 60 |

(b) A part of the crystalline product obtained in the above (a) was baked in air at about 200° C. for 1 hour. The baked product did not give a powder X-ray diffraction peak and was amorphous.

Having described our invention as related to the present embodiments, it is our intention that the invention not be limited by any of the details of the description, unless otherwise specified, but rather be construed broadly within its spirit and scope as set out in the accompanying claims.

What we claim is:

1. A crystalline aluminum organophosphate stable against heating, comprising a skeleton structure having micropores having a diameter in the range of about 0.26 to about 1.2 nm therein and represented by formula (I) in chemical composition and having a specific surface area of 40 to 600 m²/g:

formula (I):

$$[(Al_2O_3) \cdot (RPO_2)_x]$$

wherein R represents a lower alkyl group linked to a phosphorus atom, and x is such a number that $2.0 \leq x \leq 3.6$ wherein the alkyl groups constituting part of the skeleton are arranged in the pore spaces formed by an inorganic skeleton to make a wall of micropores hydrophobic and flexible.

2. The crystalline aluminum organophosphate as claimed in claim 1, wherein R in formula (I) represents a methyl group.

3. The crystalline aluminum organophosphate as claimed in claim 1, wherein the skeleton structure has uniform micropores having a diameter in the range of about 0.26 to about 1.2 nm.

4. The crystalline aluminum organophosphate as claimed in claim 1, wherein the crystalline structure is not changed by heating to at least 200° C.

5. The crystalline aluminum organophosphate as claimed in claim 1, wherein the specific surface area is 40 to 600 m²/g, after heat treatment at 200° to 600° C.

6. A crystalline aluminum organophosphate stable against heating, comprising a skeleton structure having micropores therein and represented by formula (I) in chemical composition:

formula (I):

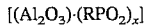

wherein R represents an alkyl group linked to the phosphorus atom, which gives a powder X-ray diffraction pattern containing at least diffraction interplanar spacings d shown in the following Table 1:

TABLE 1

| 2θ | d | Relative Intensity |
|---|---|---|
| 7.15–7.45 | 12.4–11.8 | 1000 |
| 12.5–12.8 | 7.09–6.91 | 40–300 |
| 19.2–19.5 | 4.62–4.54 | 60–250 |
| 21.85–22.15 | 4.07–4.00 | 80–300 |
| 25.25–25.55 | 3.53–3.48 | 5–50 |
| 26.35–26.65 | 3.39–3.34 | 5–50 |
| 28.4–28.7 | 3.15–3.11 | 5–50 |
| 33.7–34.0 | 2.66–2.63 | 5–50 |
| 39.15–39.45 | 2.30–2.28 | 5–50 | and wherein said x is such that $2.4 \leq x \leq 3.6$.

7. A crystalline aluminum organophosphate stable against heating, comprising a skeleton structure having micropores therein and represented by formula (I) in chemical composition:

formula (I):

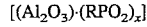

wherein R represents an alkyl group linked to the phosphorus atom, which gives a powder X-ray diffraction pattern containing at least diffraction interplanar spacings d shown in the following Table 2:

TABLE 2

| 2θ | d | Relative Intensity |
|---|---|---|
| 7.05–7.35 | 12.6–12.0 | 1000 |
| 11.35–11.65 | 7.80–7.59 | 10–50 |
| 12.25–12.55 | 7.21–7.03 | 10–50 |
| 18.85–19.15 | 4.71–4.63 | 30–200 |
| 20.9–21.2 | 4.25–4.18 | 10–50 |
| 21.6–21.9 | 4.12–4.05 | 30–200 |
| 24.8–25.1 | 3.59–3.54 | 10–50 |
| 27.9–28.2 | 3.20–3.15 | 10–50 | and wherein said x is such that $2.4 \leq x \leq 3.6$.

8. A crystalline aluminum organophosphate stable against heating, comprising a skeleton structure having micropores therein and represented by formula (I) in chemical composition:

formula (I):

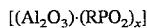

wherein R represents an alkyl group linked to the phosphorus atom, which gives a powder X-ray diffraction pattern containing at least diffraction interplanar spacings d shown in the following Table 3:

TABLE 3

| 2θ | d | Relative Intensity |
|---|---|---|
| 9.1–9.4 | 9.76–9.44 | 1000 |
| 11.3–11.6 | 7.83–7.62 | 30–200 |
| 18.3–18.6 | 4.85–4.76 | 20–100 |
| 19.9–20.2 | 4.46–4.39 | 5–70 |
| 21.4–21.7 | 4.15–4.09 | 5–70 |
| 23.7–24.0 | 3.76–3.70 | 60–250 |
| 24.0–24.3 | 3.71–3.65 | 50–250 |
| 31.7–32.0 | 2.82–2.79 | 20–150 | and wherein said x is such that $2.0 \leq x \leq 3.3$.

* * * * *